(12) United States Patent
Yang et al.

(10) Patent No.: US 6,727,081 B2
(45) Date of Patent: Apr. 27, 2004

(54) MICROORGANISM ISOLATED FROM CHINESE ELM (ULMUS SP.) AND PROCESS FOR PREPARING EXOPOLYSACCHARIDES BY EMPLOYING THE MICROORGANISM

(75) Inventors: Young Lyeol Yang, Taejon (KR); Young Joo Kim, Taejon (KR)

(73) Assignee: Samsung Electronics Co., Ltd., Kyunggi-do (KR)

( * ) Notice: Subject to any disclaimer, the term of this patent is extended or adjusted under 35 U.S.C. 154(b) by 0 days.

(21) Appl. No.: 09/921,013

(22) Filed: Jul. 27, 2001

(65) Prior Publication Data

US 2002/0115158 A1 Aug. 22, 2002

(30) Foreign Application Priority Data

Jul. 28, 2000 (KR) .......................... 2000-43675

(51) Int. Cl.$^7$ ............................ C12P 19/04; C12N 1/20; A01N 63/00; A01N 63/02; A61K 37/715
(52) U.S. Cl. .................... 435/101; 435/252.1; 435/822; 424/93.4; 514/54
(58) Field of Search .............. 435/101, 252.1, 435/822; 424/93.4; 514/54

(56) References Cited

U.S. PATENT DOCUMENTS

| 4,578,458 | A | | 3/1986 | Pier |
| 4,806,636 | A | * | 2/1989 | Harris et al. |
| 5,360,737 | A | * | 11/1994 | Ishii et al. |

OTHER PUBLICATIONS

Kimmel et al., *Optimization of Exopolysaccharide Production by Lactoballus delbrueckii subsp. Bulgaricus RR Grown in a Semidefined Medium*, Appl. Environ. Microbio., 64(4):659–664 (1998).

Shimada et al., *Acidic Exopolysaccharide Produced by Enterobacter sp.*, J. Fermentation and Bioengineering, 84(2):113–118 (1997).

Jann et al., *NMR Reinvestigation of the Capsular K27 Polysaccharide (K27 Antigen) from Escherichia coli 08:K27:H*, Carbohydrate Research, 227:353–358 (1995).

Takeda et al., *Separation and Preliminary Characterization of Acidic Polysaccharides Produced by Enterobacter sp.*, J. Ferm. Bioeng, 78(2):140–144 (1994).

Ivanova et al., *Isolation of a Polysaccharide with Antiviral Effect from Ulva lactuca*, Preparative Biochemistry, 24(2)83–97 (1994).

Quesada et al., *Comparative Methods for Isolation of Volcanella eurihalina Exopolysaccharide*, Biotechnology Techniques, 8(10):701–706 (1994).

Morin et al., *Effect of Carbon, Nitrogen, and Agitation of Exopolysaccharide Production by Enterobacter agglomerans Growth on Low–grade Maple Sap*, Enzyme Microb. Technol., 15:500–507 (1993).

Roller et al., *Biotechnology in the Production and Modification of biopolymers for Foods*, Critical Reviews in Biotechnology, 12(3):261–277 (1992).

Franz, *Polysaccharides in Pharmacy: Current Applications and Future Concepts*, Planta Medica, 55:493–497 (1989).

Yalpani, *Commercial Polysaccharides: Recent Trends and Developments*, Elsevier Science Publishers B V., Amsterdam (1987).

Scheepe–Leberkuhne et al., *Optimization and Preliminary Characterization of an Exopolysaccharide Synthesis by Enterobacter sakazakii*, Biotechnology Letters. 8(10)695–700 (1986).

Sutherland, *Microbial Exopolysaccharides–Structural Subtleties and their Consequences*. Pure & Appl. Chem., 69(9):1911–1917 (1997).

* cited by examiner

Primary Examiner—Vera Afremova
(74) Attorney, Agent, or Firm—Knobbe, Martens Olson & Bear LLP

(57) ABSTRACT

The present invention relates to a novel Enterobacter sp. strain SSYL deposited under accession number KCTC 0687BP isolated from the root bark of Chinese elm, which produces immunostimulating exopolysaccharides with anticancer activity, a process for preparing the exopolysaccharides by fermenting the said microorganism in a culture medium, exopolysaccharides prepared by the process and their uses thereof. The exopolysaccharides of the invention have a molecular weight of 100,000 to 1,000,000 and consist of 40–75% of total sugar, 5–15% of total acidic sugar and 10–25% of total protein. The exopolysaccharides exhibits a high immunoenhancing activity in immune cell proliferation, direct mitogenicity and mixed lymphocyte reaction, and further a high anticancer activity in vivo by virtue of immunostimulation. Moreover, the production of the exopolysaccharides by fermentation of a microorganism, makes it possible to provide the exopolysaccharides with a uniform quality and mass production without destruction of the plant species. The exopolysaccharides of the subject invention have practical uses as an active ingredient for anticancer agents, immunoenhancers and foodstuffs.

11 Claims, 12 Drawing Sheets

MICROORGANISM ISOLATED FROM CHINESE ELM (ULMUS SP.) AND PROCESS FOR PREPARING EXOPOLYSACCHARIDES BY EMPLOYING THE MICROORGANISM

BACKGROUND OF THE INVENTION

1. Field of the Invention

The present invention relates to a novel microorganism isolated from Chinese elm(Ulmus sp.) and a process for preparing immunostimulating exopolysaccharides with anticancer activity by employing the microorganism, more specifically, to a novel Enterobacter sp. isolated from the root bark of Chinese elm(Ulmus sp.) alive, which produces immunostimulating exopolysaccharides with anticancer activity, a process for preparing the exopolysaccharides by culturing the microorganism, the exopolysaccharides thus prepared and novel practical uses thereofs.

2. Description of the Related Art

Polysaccharides have been produced from natural products such as plants and seaweeds, or microorganisms and widely used for the materials for foodstuffs, medicine, etc. In light of the various uses of polysaccharides, intensive research has been actively undertaken to produce polysaccharides with novel structure and sugar composition, and to explore their potential uses.

Recently, it has been reported that polysaccharides existing in exterior of cell wall play an important role as a messenger for signal transduction between cells, which arouse great interests in polysaccharides. Examples of commercialized exopolysaccharides produced by microorganisms include xanthan gum, pullulan, gellan gum, curdlan, hyaluronic acid, etc.

Meanwhile, in Korea and China, Chinese elm (elm tree as common name) had been used for a long time as a therapeutic agent, as well as for relieving famine. The root bark of Chinese elm has been used in a dried form for oriental medicine or folk remedy, and its pharmacological properties are described in ancient literatures of oriental medicine such as Bonchogangmok, Euhakibmoon, Hyangyakjibsungbang, and Dongeubogam. According to such medical literatures, the root bark of Chinese elm is known to be a powerful remedy for a rash and an abscess, effective on gastric ptosis, gastric ulcer, and duodenal ulcer, and also working on a mild stomachache, a digestive disorder, urinating disorder, empyema, otitis media, an abscess, a festered wound such as a swelling and a boil, skin conditioning, and uterine- and breast-associated diseases.

In this connection, the present inventors also found that water-soluble polysaccharides(proteoglycans) extracted from the root bark of Chinese elm have an anticancer activity by immunostimulation.

However, it has been revealed that water-soluble polysaccharides(proteoglycans) extracted from the root bark of Chinese elm may bring about destruction of the plant species and their qualities cannot be controlled in an efficient manner owing to different compositions depending on the area and timing of taking the plants.

Under the circumstances, there are strong reasons for exploring and developing alternative process for preparing the exopolysaccharides of uniform quality in a massive manner.

SUMMARY OF THE INVENTION

The present inventors have made an effort to solve the problems mentioned above, and isolated a novel microorganism of Enterobacter sp. which produces exopolysaccharides with immunostimulating activity, from the root bark of Chinese elm. Furthermore, they found that: the exopolysaccharides produced by fermentation of the said microorganism possess an anticancer activity by immunostimulation which is similar to physiological activity of the water-soluble polysaccharides(proteoglycans) extracted from the root bark of Chinese elm; and, their mass production can be accomplished with a uniform quality by controlling medium and culture conditions, without destruction of the plant species.

One aspect of the present invention is to provide an isolated microorganism identified by accession number KCTC 0687BP.

Another aspect of the present invention provides a method of producing an exopolysaccharide. The method comprises the steps of providing an isolated microorganism identified by accession number KCTC 0687BP, and culturing the microorganism in a medium so as to allow production of an exoploysaccharide. The method further comprises isolating the exopolysaccharide from a mixture comprising the culture medium, the microorganism and the exopolysaccharide. The culture medium comprises a carbon source selected from the group consisting of glucose, sucrose, fructose, rhamnose, galactose, arabinose, mannitol, lactose, gluconate, xylose and mixtures thereof. The culturing is performed at a temperature ranged from about 25° C. to about 38° C. under aeration at a flow rate ranged from about 0.1 vvm to about 1.5 vvm and under agitation at an agitation speed ranged from about 150 to about 500 rpm. The isolation of the exopolysaccharide comprises: removing cells from the culture mixture; and dialyzing a resulting mixture so as to isolate the exopolysaccharide. The isolation further comprises lyophilizing the separated exopolysaccharide. The removal of cells comprises: centrifuging the culture mixture to obtain a supernatant; precipitating a mixture comprising the exopolysaccharide; dissolving the precipitate in a liquid; and removing remaining cells. The present invention further provides a composition obtainable by the method.

Another aspect of the present invention provides a composition comprising an isolated exopolysaccharide from an Enterobacter species, wherein the species is obtained from root bark of Chinese elm, Ulmus species and the exopolysaccharide has a molecular weight ranged from about 100,000 to about 1,000,000. The isolated exopolysaccharide comprises sugar in an amount ranged from about 40 wt. % to about 75 wt. %. The isolated exopolysaccharide comprises acidic sugar in an amount ranged from about 5 wt. % to about 15 wt. %. The isolated exopolysaccharide comprises protein in an amount ranged from about 10 wt. % to about 25 wt. %. The isolated exopolysaccharide comprises glucose, fructose, galactose, fucose and glucuronic acid. The isolated exopolysaccharide comprises 10–30 wt. % glucose, less than 1 wt. % fructose, 10–15 wt. % galactose, 8–12 wt. % fucose and 40–70 wt. % glucuronic acid.

Still another aspect of the present invention provides a method of inducing immune cell proliferation, which comprises providing cells and contacting the exopolysaccharide with the cells, thereby stimulating proliferation of immune cells. The method further comprises identifying immune cells in need of an induction of proliferation and/or measuring immune cell proliferation.

Still another aspect of the present invention provides a method of inhibiting proliferation of cancer cells. The method comprises providing a cancer cell and contacting the exopolysaccharide with the cancer cell. The cancer cells comprising melanoma cells.

Still further aspect of the present invention provides a method of inhibiting cancer cell proliferation in a mammal. The method comprises identifying a mammal in need of an agent that inhibit cancer cell proliferation and providing the mammal with the expolysaccaharide.

BRIEF DESCRIPTION OF THE DRAWINGS

The above, the other objects and features of the invention will become apparent from the following descriptions given in conjunction with the accompanying drawings, in which.

DETAILED DESCRIPTION OF THE INVENTION

Figure 1:
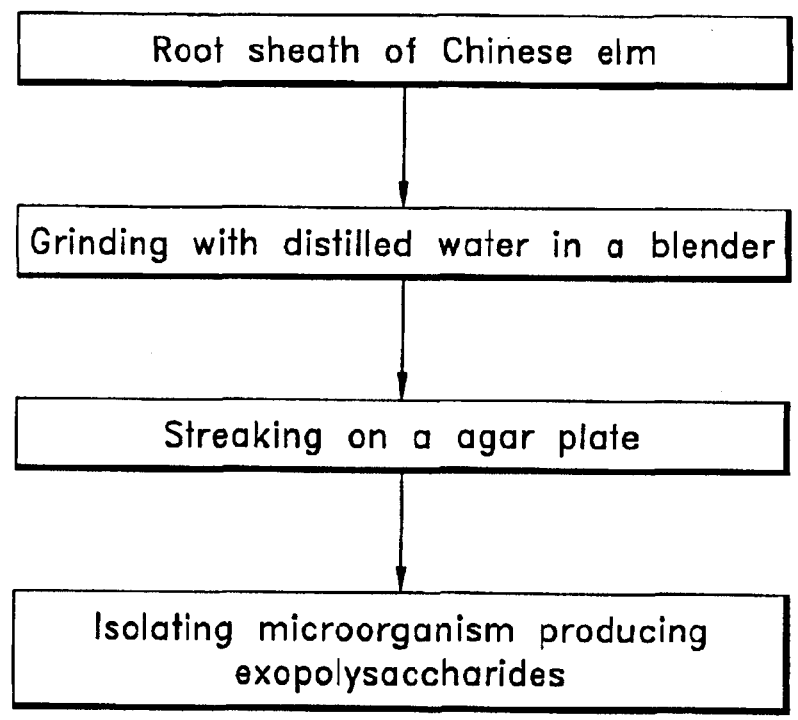
FIG. 1 is a schematic representation of the process for isolating a microorgnism from the root bark of Chinese elm.

The present inventors isolated a microorganism producing exopolysaccharides from the root bark of Chinese elm, which was identified as a novel microorganism which belongs to Enterobacter sp. In this regard, the microorganism was named "Enterobacter sp. SSYL", and deposited with the Korean Collection for Type Cultures (KCTC, #52, Oun-dong, Yusong-ku, Taejon, Republic of Korea) affiliated with the Korea Research Institute of Bioscience and Biotechnology (KRIBB), an international depository authority, under accession (deposition) No. KCTC 0687BP on Nov. 3, 1999.

The said microorganism was cultured in a variety of media containing MYGP (composed of malt extract, yeast extract, glucose, and bactopeptone), at a temperature of 25–38° C., under an agitation speed of 150–500 rpm, pH 4.0–7.5 and an aeration flow rate of 0.1–1.5 vvm to produce exopolysaccharides, which was subsequently isolated and purified, preferably, followed by lyophilization. The culture medium comprises a carbon source such as glucose, sucrose, fructose, rhamnose, galactose, arabinose, mannitol, lactose, gluconate, xylose, and mixture thereofs.

For the preparation of the exopolysaccharides, the microorganism is cultured in a medium to produce exopolysaccharides, and then, the exopolysaccharides are isolated from the culture, which comprises the steps of: centrifuging the culture to obtain a supernatant; adding an organic solvent such as acetone, ethanol, methanol or propanol to the supernatant at a ratio of 1:1–1:5 (v/v), preferably, a ratio of 1:2–1:3 (v/v), to give a precipitate; dissolving the precipitate in distilled water and removing remaining cells by filtration or centrifugation; and, dialyzing the resultant against a membrane with 4,000–14,000 MWCO to discard residual saccharides and low molecular weight materials. After dialysis, filtration or centrifugation may be further carried out to remove remaining cells, if necessary.

Exopolysaccharides thus produced have a molecular weight of 100,000 to 1,000,000 and consist of 40–75% of total sugar, 5–15% of total acidic sugar and 10–25% of total protein. Compositions and contents of sugars in the exopolysaccharides are 10–30% glucose, less than 1% fructose, 10–15% galactose, 8–12% fucose and 40–70% glucuronic acid.

In the course of isolating exopolysaccharides from the culture, biological process employing enzymes such as trypsin, pepsin and papain, or chemical process employing chemicals such as trichloroacetic acid may be additionally applied to remove protein impurities in the exopolysaccharides.

Changes in intrinsic viscosity of the exopolysaccharide depending on concentration and pH have been studied, and a comparison of rheological properties of the exopolysaccharide with those of xanthan gum has been made to find out the exopolysaccharide of the invention has similar pseudoplastic rheological properties to commercially available xanthan gum.

Further, the investigations for anticancer activity by immunostimulation, employing exopolysaccharides produced by the said fermentation, were intended to propose their uses possible on the basis of their experimental results. Anticancer activity by immunostimulation of the exopolysaccharide has been determined by immunostimulating assays in vitro (immune cell proliferation, mixed lymphocyte reaction and direct mitogenicity for immune cells), and by immunostimulating assays in vivo (test of acute toxicity in a septic shock model system, and anticancer activity assay in a B16 melanoma model system).

In these experiments, the exopolysaccharides exhibited high immunostimulating activities in assays for immune cell proliferation, mixed lymphocyte reaction, and direct mitogenicity, moreover, survival rate of melanoma mice increased by 138.1% at a dose of 0.3 mg/kg in assays for anticancer activity in vivo, by virtue of immunostimulation. On the other hand, it has been observed and reported that the anticancer activity of the water-soluble polysaccharides (proteoglycans) extracted from root bark of Chinese elm increases by 139.2% in survival rate of melanoma mice at a dose of 3 mg/kg. Thus, it was found that with a 1/10 concentration the immunostimulating anticancer activity of the exopolysaccharide derived from the microorganism of the invention was similar to those of the said water-soluble polysaccharides (proteoglycans) extracted from the root bark of Chinese elm.

Therefore, the present invention provides practical uses of the exopolysaccharides for anticancer agents, immunoenhancers and foodstuffs as an active ingredient. Besides such specific uses, the exopolysaccharide of the invention may be used for general purposes of polysaccharides such as emulsifier, stabilizer, adhesive, coagulant, agglutinating agent, lubricant, film-forming agent, thickener, suspending agent, and other industrially important polymer mediators.

Anticancer agents or immunostimulants comprising the exopolysaccharides of the invention as an active ingredient may be sujected to enteral (oral or inhaled) or parenteral (nonoral) (e.g., intravenous, subcutaneous, transcutaneous and rectal) administration, and the said agents may be prepared depending on purposes, in various preparations such as tablets, capsules, granules, powders, suppositories, ointments, injections, emulsions, suspensions, and syrups. The said various formulations may be prepared by conventional methods using nontoxic additives such as excipient, binder, disintegrator, lubricant, preservative, antioxidant, isotonic agent, buffer, coating agent, sweetener, solubilizer, base, dispersant, stabilizer, coloring agent, etc. Examples of nontoxic additives available are listed below.

First, excipients include starch and its derivatives (dextrin, carboxymethylstarch, etc.), cellulose and its derivatives (methylcellulose, hydroxypropylmethylcellulose, etc.), saccharides (lactose, sucrose, glucose, etc.), silicic acid and silicates (natural aluminium silicate, magnesium silicate, etc.), carbonates (calcium carbonate, magnesium carbonate, sodium bicarbonate, etc), aluminium hydroxide, magnesium, synthetic hydrotalcite, polyoxyethylene derivatives, glycerine monostearic acid, sorbitan monooleic acid, etc.

Binders include starch and its derivatives (α-starch, dextrin, etc.), cellulose and its derivatives (ethyl cellulose, sodium carboxymethyl cellulose, hydroxypropylmethyl cellulose, etc.), gum arabic, gum tragacanth, gelatin, saccharides (glucose, sucrose, etc.), ethanol, polyvinylalcohol, etc.

Disintegrators include starch and its derivatives (carboxymethyl starch, hydroxypropylmethyl starch, etc.), cellulose and its derivatives (sodium carboxymethyl cellulose, hydroxypropylmethyl cellulose, etc.), carbonates (calcium carbonate, calcium hydrogen carbonate, etc.), gum tragacanth, gelatin, sugars, etc.

Lubricants include stearic acid, calcium stearate, magnesium stearate, talc, silicic acid and silicates (rigid silica, natural aluminium silicate, etc.), titanium oxide, calcium hydrogen phosphate, dried aluminium hydroxide gel, etc.

Preservatives include p-hydroxybenzoate, sulfites (sodium sulphite, sodium pyrosulfites, etc.), phosphates (sodium phosphate, poly (calcium phosphate), poly (sodium phosphate), sodium metaphosphate, etc.), alcohols (chlorobutanol, benzylalcohol, etc.), benzalconium chloride, benzetonium chloride, phenol, cresol, cresol chloride, dihydroacetic acid, sodium dihydroacetate, glycerin sorbic acid, sugars, etc.

Antioxidants include sulfites (sodium sulfite, sodium hydrogen sulfite, etc.), rongalite, erythorbic acid, L-ascorbic acid, cysteine, thioglycerol, butyl hydroxy anisol, dibuthylhydroxy toluene, propylgallic acid, ascorbylpalmitate, dl-α-tocopherol, etc.

Isotonic agents include sodium chloride, sodium nitrate, potassium nitrate, dextrin, glycerin, glucose, etc.

Coating agents include cellulose derivatives (hydroxypropyl cellulose, celluloseacetate phthalate, hydroxypropylmethyl cellulose phthalate, etc.), shellac, polyvinylpyrolidon, polyvinylpyridine (poly-2-vinypyridine, poly-2-vinyl-5-ethylpyridine, etc.), polyvinylacetyl diethylaminoacetate, polyvinylalcohol phthalate, methacrylate, methacrylate copolymer, etc.

Sweeteners include saccharides (glucose, lactose, sucrose, etc.), sodium saccharin, sugar alcohol, etc.

Solubilizers include ethylenediamine, nicotinamide, sodium saccharin, citric acid, citrate, sodium benzoate, soaps, polyvinylpyrrolidone, polysorbate, sorbitan, fatty acid ester, glycerin, propyleneglycol, benzylalcohol, etc.

Bases include lipid (lard, etc.), vegetable oil, animal fat, lanolin acid, petrolatum, paraffin, wax, resin, bentonite, glycerin, glycol oil, high alcohol (stearylalcohol, cetanol, etc.), etc.

Dispersants include gum arabic, gum tragacanth, cellulose derivatives (methyl cellulose, etc.), stearic acid polyester, sorbitan sesquioleate, aluminium monostearate, sodium alginate, polysorbate, sorbitan fatty acid ester, etc.

Stabilizers include sulfites (sodium hydrogen sulfite, etc.), nitrogen, carbon dioxide, etc.

In the preparation of the pharmaceutical formulations, the content of the exopolysaccharides of the invention, may differ according to the type of formulations, but in general is 0.01 to 100 wt %.

Dosage level of anticancer agents or immunostimulants of the invention may vary in a wide range depending on the kinds of warm-blood animals to be treated, including a human, the progress of disease, the decision of doctor, etc. However, the effective dosage may be determined within the range from 0.01 to 30 mg/kg (based on the exopolysaccharides or their pharmaceutically acceptable salts) for an enteral administration, and within the range from 0.01 to 10 mg/kg for parenteral administration, per day for a 60 kg adult. The daily dose mentioned above may be administered once a day or divided into several doses, which may be optionally changed depending on the progress of the disease and doctor's decision.

The present invention is further illustrated in the following examples, which should not be taken to limit the scope of the invention.

EXAMPLE 1

Isolation and Identification of a Novel Microorganism Producing Exopolysaccharides from Root Bark of Chinese Elm.

The root of Chinese elm was picked from a hill near Kimhae, Wando arboretum, and Cheongsando, Korea. After removing soil from the root, the bark was taken off, chopped, and throughly ground with distilled water in a blender. During this process, water-soluble polysaccharides were extracted and the solution became viscous. The viscous solution was streaked on a solid agar medium of MYGP (malt extract 3 g/L, yeast extract 3 g/L, glucose 10 g/L, bactopeptone 5 g/L).

After incubating for about 2 days at 30° C., colonies producing exopolysaccharides were isolated from various colonies on a solid agar medium. The isolated colonies were checked for production of exopolysaccharides in MYGP liquid medium (100 ml) under a condition of 30° C. and 200 rpm, and the strain with the highest yield was isolated and identified. Identification of the strain was performed at the Collection for Type Cultures (KCTC) affiliated with the Korea Research Institute of Bioscience and Biotechnology (KRIBB), an international depository authority, with various analysis methods such as fatty acid analysis (MIDI), API 20E analysis, BIOLOG analysis, and 16S rRNA sequencing. FIG. 1 is a schematic representation of the isolation process of microorganism producing exopolysaccharides from the root bark of live Chinese elm.

Upon overall consideration of the above-mentioned analyses, the said microorganism producing exopolysaccharides was identified as a novel strain belonging to Enterobacter sp. Therefore, the present inventors named the identified bacterial strain "Enterobacter sp. SSYL", and deposited with the Korean Collection for Type Cultures (KCTC, #52, Oun-dong, Yusong-ku, Taejon, Republic of Korea) affiliated with the Korea Research Institute of Bioscience and Biotechnology (KRIBB), an international depository authority, under accession (deposition) No. KCTC 0687BP on Nov. 3, 1999.

EXAMPLE 2

Production of Exopolysaccharides Employing a Novel Microorganism, Enterobacter sp. SSYL (KCTC 0687BP)

In order to produce exopolysaccharides by fermentation using the novel microorganism isolated in Example 1, Enterobacter sp. SSYL was cultured under a condition described below: That is, the medium comprising 60 g of carbon source, 6 g of malt extract, 6 g of yeast extract, and 10 g of bactopeptone was added into a 2 L fermentor (Model MDL 6C, Marubishi Co. Ltd., Japan), where glucose was used as a carbon source. A culture condition employed was 30° C., 250 rpm, 0.25–1.0 vvm of air flow, and approximately one day of culture time.

After fermentation, cells were removed from culture medium by ultracentrifugation (Sorvall RC 26 Plus, Rotor SLA-1500, U.S.A.) at 12,000 rpm for 20 minutes to obtain supernatant. To the supernatant, acetone was added in the ratio of 1:2 (v/v) and a precipitate containing exopolysaccharide was isolated from the supernatant. The isolated precipitate was redissolved in 1.5–2 L of distilled water and then filtered under pressure on a filter paper (pore size: 0.7–1.6 $\mu$m). The filtrate was dialyzed in the dialysis membrane with 6,000–8,000 MWCO against distilled water for approximately one day. Subsequently, dialyzed solution was freeze-dried to obtain white dried exopolysaccharide. The final yield of exopolysaccharide against carbon source was 10% or so.

Figure 2:
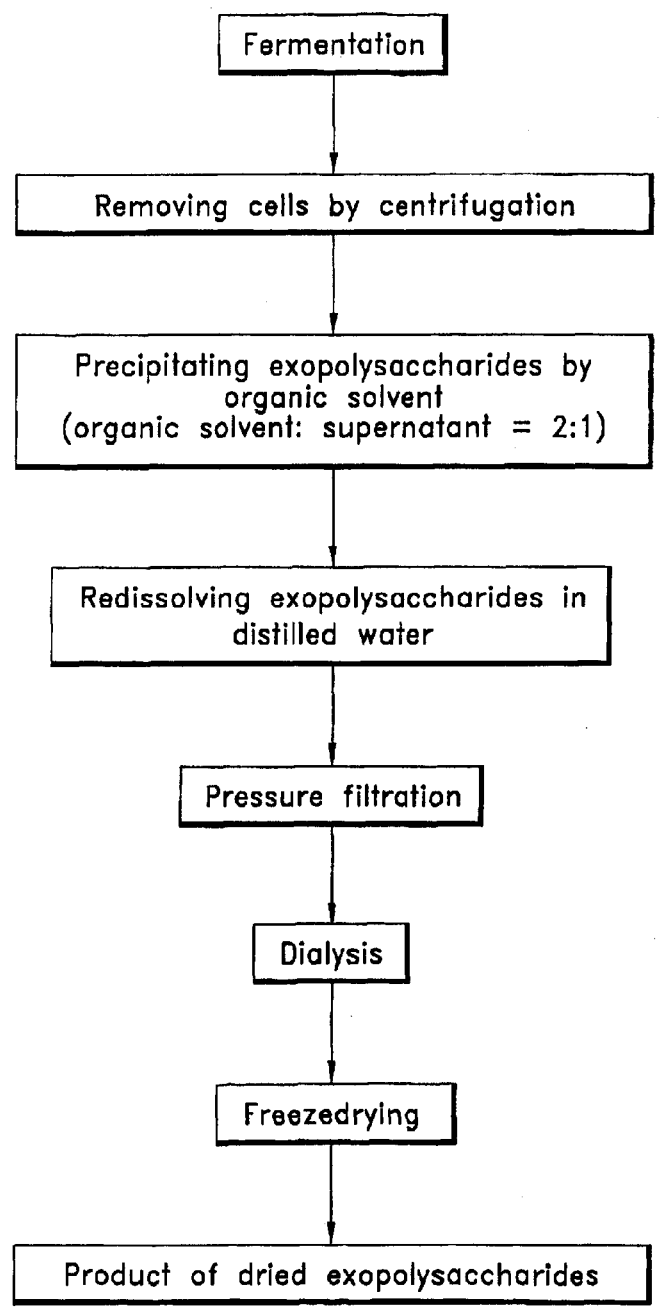
FIG. 2 is a schematic representation of the process for preparing the exopolysaccharide by fermentation of a novel microorganism.
Figure 3:
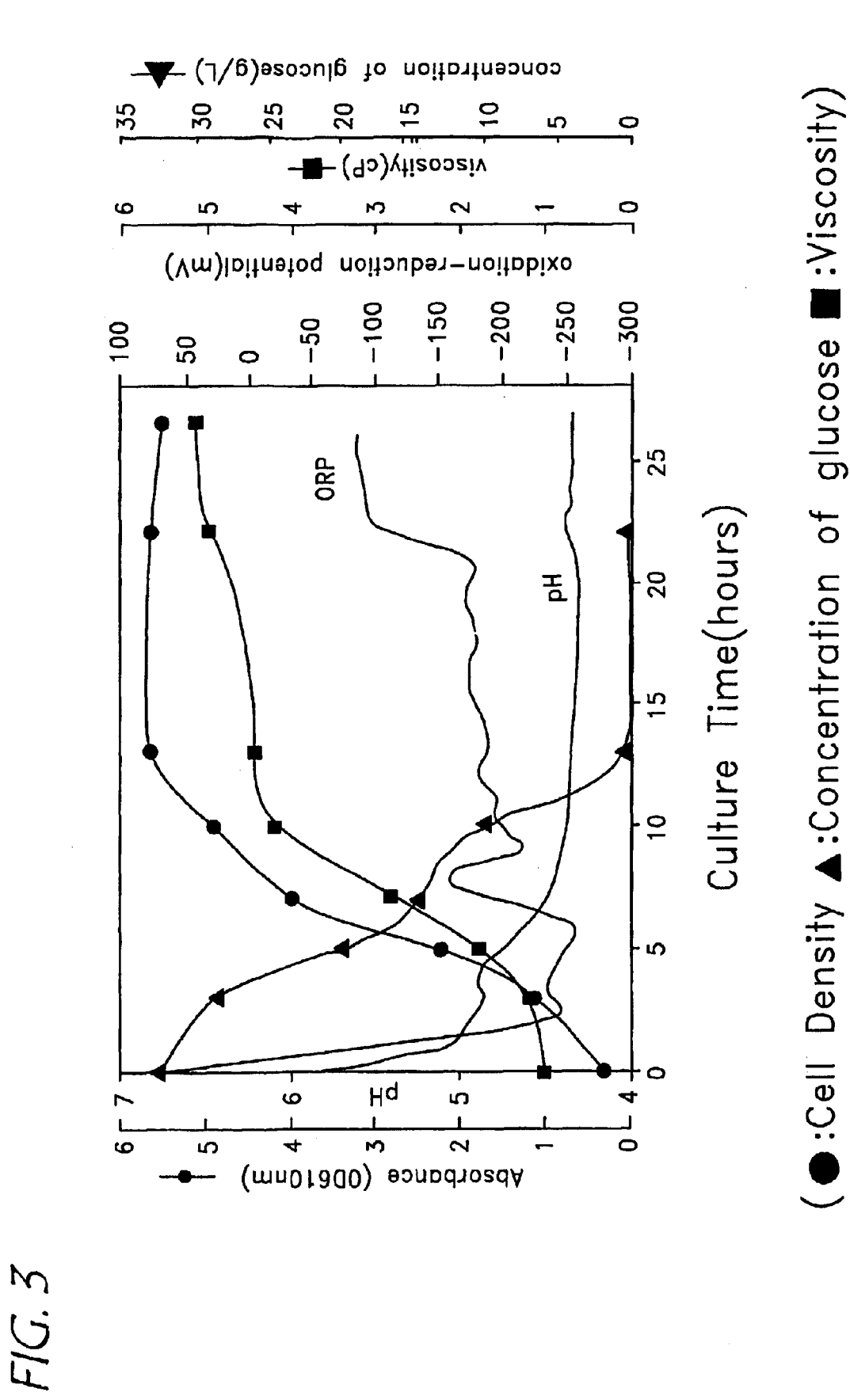
FIG. 3 is a graph showing a profile of batch fermentation of the microorganism producing exopolysaccharide.

The process for preparing exopolysaccharide by fermentation of novel microorganism described above is outlined in FIG. 2. FIG. 3 is a graph showing a profile of batch fermentation using glucose as a carbon source.

EXAMPLE 3

Chemical Analysis of Exopolysaccharide

EXAMPLE 3-1

Molecular Weight Determination of Exopolysaccharide

The molecular weight of exopolysaccharide was determined by HPLC with Tosohaas TSK-Gel G-3000SW gel filtration column (7.5 mm in diameter, 600 mm in length, Japan) and 0.2 M ammonium acetate containing 20 mM phosphate (pH 6.8) as a mobile phase at a flow rate of 10 ml/min. As the size markers for gel filtration chromatography, apoferritin (443 kDa), β-amylase (200 kDa), alcohol dehydrogenase (150 kDa), albumin (66 kDa), carboxylate dehydrogenase (29 kDa), cytochrome C (12.4 kDa), and dextran (2,000 Da) were used. After determination of void volume (hereinafter referred to as 'Vo') by passing dextran through the column and elution volume (hereinafter referred to as 'Ve') by passing standard materials (6 kinds of materials used as size markers except dextran) through the column, a standard curve of molecular weight vs. Ve/Vo was prepared. Following the measurement of Ve of exopolysaccharide, Ve/Vo was calculated to detemine molecular weight of exopolysaccharide, thus, it has been determined that the exopolysaccharide is a macromolecule with a molecular weight range of 100–1,000 kDa.

EXAMPLE 3-2

Determination of Total Sugar Content of the Exopolysaccharide

Total sugar content of the exopolysaccharide was determined by phenol-sulfuric acid reaction. That is, 0.2 ml of 5% (w/v) phenol in distilled water was added to 0.2 ml of 50 $\mu$g/ml exopolysaccharide in distilled water and then the mixture was shaken, to which 1.0 ml of 98% sulfuric acid was added, followed by incubating for 10 minutes, shaking, incubating for 30 minutes, and then sugar content was determined by measuring absorbance at 485 nm. A standard concentration curve was prepared using glucose solution (5, 10, 50, 100, and 500 $\mu$g of glucose was dissolved respectively, per ml of distilled water) as the standard sugar solution, and the sugar content of exoplysaccharide was determined as 56.9±19.7%. As a reference, when sucrose was used as a carbon source, the sugar content of exoplysaccharide was 52.9±2.26%.

EXAMPLE 3-3

Analysis of Compositions and Contents of Sugar in the Exoplysaccharide

To analyze sugar compositions and their contents of the exopolysaccharides, 8 mg of exopolysaccharide treated with 0.8 ml of 2 M HCl was hydrolyzed at 100° C. for 2–5 hours, and then the reaction mixture was neutralized with barium carbonate, followed by centrifugation to obtain a supernatant, which was subject to HPLC analyses. HPLC analysis was performed with an preparatory column (Waters Carbohydrate column, 4.6 mm in diameter, 250 mm in length, U.S.A.) and an aqueous solution of 75% (v/v) acetonitrile as a mobile phase at a rate of 0.5 ml/min. After 0.5 M NaOH solution was run through the column, an electrochemical detection was carried out. Standard concentration curves of monosaccharides were prepared using standard solutions of glucuronic acid, rhamnose, arabinose, glucose, galactose, fucose, and fructose in distilled water with concentration range of 0.2–10 mg/ml, respectively.

After all, sugar compositions and their contents of the exopolysaccharide were identified to be 46.7% glucuronic acid, 10.8% fucose, 0.2% fructose, 29.9% glucose, 11.0% galactose and about 1.3% unidentified materials. Sugar compositions of the exopolysaccharide produced by Enterobacter sp. reported in the literatures were compared with those produced by the novel microorganism of the invention and the results are summarized in Table 1 below. As shown in Table 1, the sugar compositions of the exopolysaccharides produced by the novel microorganism isolated from root bark of Chinese elm have been demonstrated to be different from those produced by the microorganisms reported in literatures.

TABLE 1

Comparison of sugar compositions of the expolysaccharides produced by various Enterobacter sp.

| Microorganism | Sugar Compositions of the Exopolysaccharides |
| --- | --- |
| Enterobacter sp. | Glucose, mannose, rhamnose, fucose, glucuronic acid, galacturonic acid |
| A. E. sakazakii | Glucose, galactose, fructose, glucuronic acid, acetic acid |
| B. E. agglomerans | Glucose, galactose |
| C. E. cloacae | Glucose, galactose, fucose, glucuronic acid, pyruvic acid, acetic acid |
| Enterobacter sp. | Glucose, fucose, glucuronic acid |
| Enterobacter sp. SSYL(KCTC 0687BP) | Glucose, fructose, fucose, galactose, glucuronic acid |

EXAMPLE 3-4
Determination of Acidic Sugar Content of the Exopolysaccharide

Acidic sugar content of the exopolysaccharide was determined with the analysis for uronic acid by cabazole method. That is, 50 μg of exopolysaccharide was mixed with 1.5 ml of $NaBH_4/c.H_2SO_4$ (100 ml of 98% sulfuric acid containing 0.9 g of $NaBH_4$) on an ice bath with slow shaking followed by vigorous shaking, and then the reaction was continued for 10 minutes in boiling water. After cooling to room temperature, 50 μl of carbazole/anhydrous ethanol (10 ml of anhydrous ethanol containing 10 mg of carbazole) was added to the reaction mixture, which was, then, heated again in boiling water for 15 minutes, cooled down and analyzed spectroscopically at 525 nm. Glucuronic acid standard curve was prepared using glucuronic acid solutions at concentrations of 15, 30, and 50 μg/ml in distilled water, respectively, and acidic sugar content of the exopolysaccharide was calculated to be 9.26±3.03%. As a reference, when sucrose was used as a carbon source, acidic sugar content of exoplysaccharide was 11.8±0.85%.

EXAMPLE 3-5
Determination of Protein Content of the Exopolysaccharide

Protein content of the exopolysaccharide was determined by the Lowry method with minor modifications: That is, 0.2 ml of 0.85% (w/v) NaCl solution containing 500 μg/ml of exopolysaccharide was mixed with 2.2 ml of Biuret reagent, to which 0.1 ml of Folin-Ciocalteu's reagent was added. After incubation for 30 minutes at room temperature, the reaction mixture was analyzed spectroscopically at 725 nm. Bovine serum albumin standard curve was prepared using BSA solutions at concentrations of 250, 500, 750, and 1000 μg/ml in 0.85% (w/v) NaCl solution, respectively, and the protein content of the exopolysaccharide was calculated to be 19.9–0.92%. As a reference, when sucrose was used as a carbon source, protein content of exopolysaccharide was 16.9±2.05%.

Figure 4:
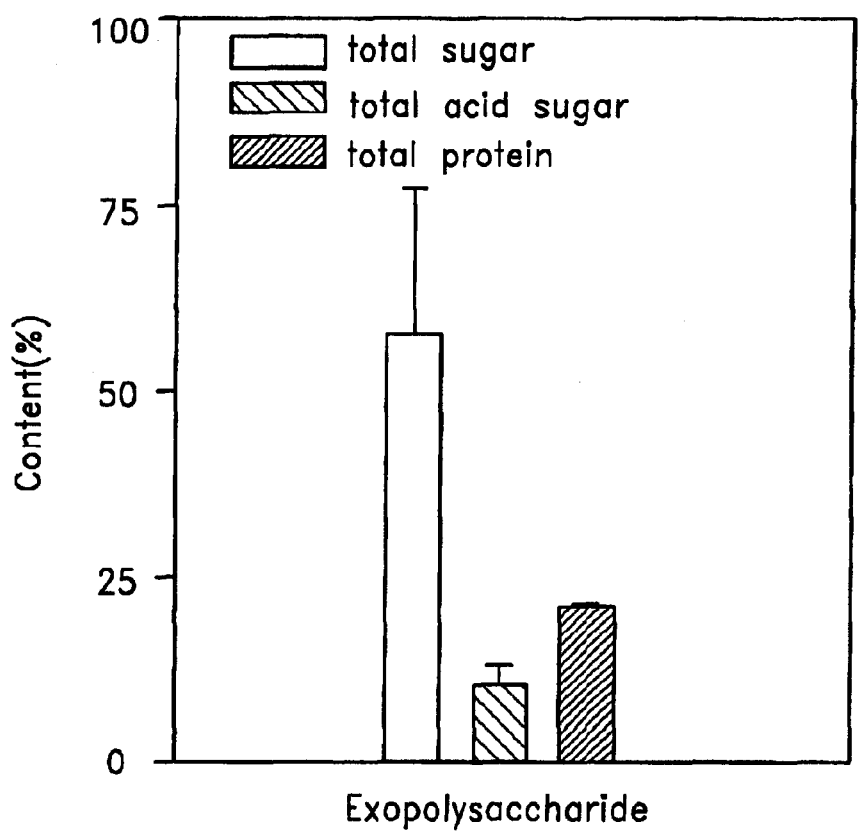
FIG. 4 is a graph showing the composition and the content of each component in the exopolysaccharide of the invention.

The results above, sugar content, acidic sugar content, and protein content of the exopolysaccharide are shown in FIG. 4.

EXAMPLE 3-6
Changes in Intrinsic Viscosity of the Exopolysaccharide Depending on Concentration and pH, and Comparison of Theological Properties of Exopolysaccharide with those of Xanthan Gum The intrinsic viscosities of the exopolysaccharide produced by using sucrose as a carbon source were measured at different concentrations with Hakke viscometer (see: Table 2). The spindle used was S51 and the temperature was 25° C.

TABLE 2

Intrinsic viscosity depending on the concentration of the exopolysaccharide

| Concentration of the Exopolysaccharide (mg/ml) | Viscosity(cP) |
| --- | --- |
| 1.1 | 4.4 |
| 9.5 | 260 |
| 15.4 | 9200 |

To investigate the pH dependency of the intrinsic viscosity, acid or base was added to the 0.5% (w/v) exopolysaccharide solution and the viscosities were measured (see: Table 3). Initial pH of the 0.5% (w/v) exopolysaccharide solution was 4.1 which belongs to acidic range.

TABLE 3 pH dependency of the viscosity

| PH | Viscosity(cP) |
| --- | --- |
| 2.68 | 76.5 |
| 4.10 | 79.6 |
| 7.52 | 63.8 |
| 11.5 | 50.3 |

As clearly demonstrated in Table 3 above, the viscosity of exopolysaccharide reached its maximum level at around pH 4, and then decreased gradually with increasing pH. Accordingly, there is a considerable discrepancy between such result of the present invention and the previous report (see: J. of Ferment. Bioeng., 84:13–18, 1997) which showed the viscosity of exopolysaccharide produced by Enterobacter sp. gradually increased with increasing pH up to 12, above which it decreased abruptly due to hydrolysis of polysaccharide.

Figure 5:
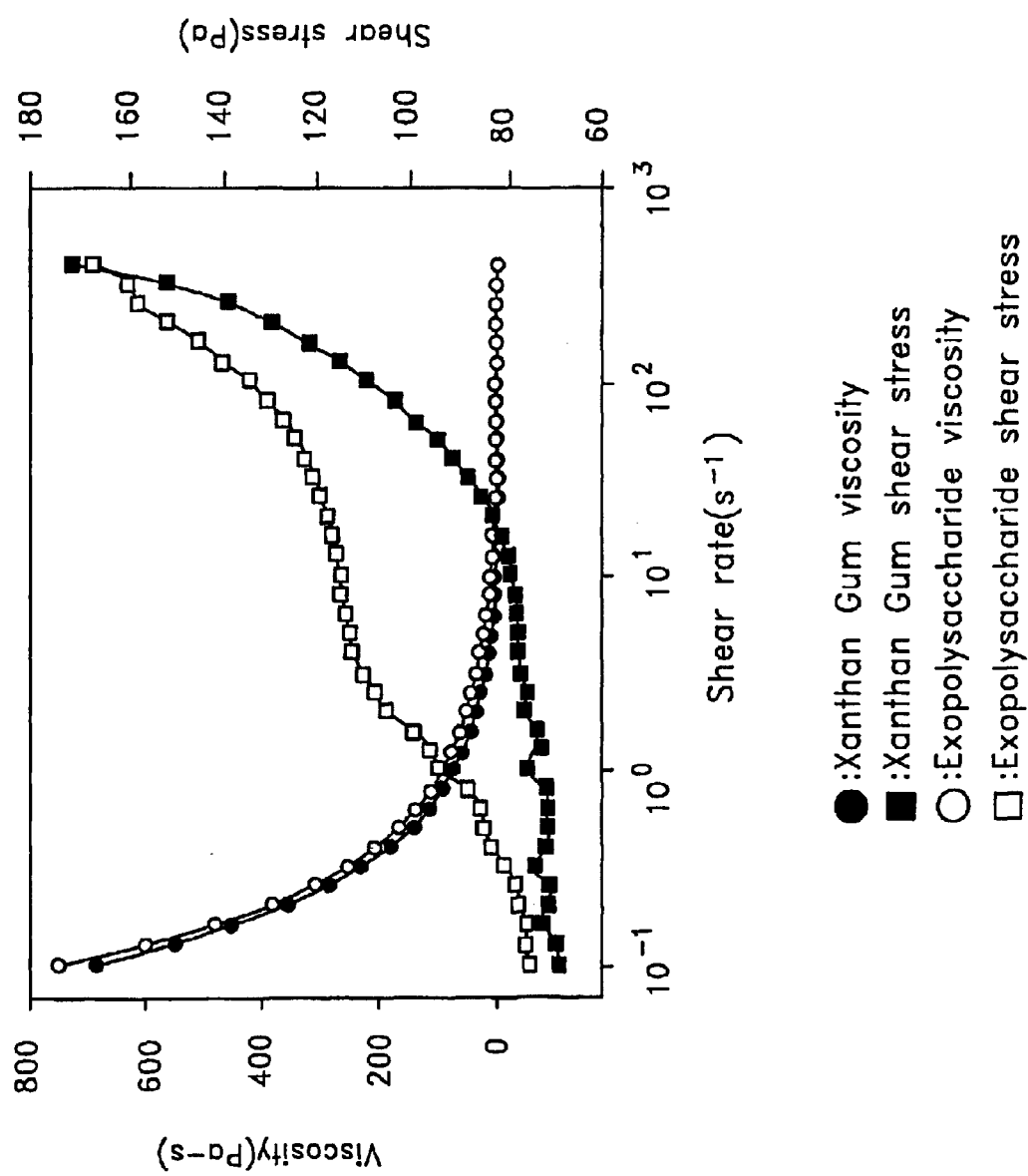
FIG. 5 is a graph showing the comparison of rheological properties between the exopolysaccharide and xanthan gum.

In order to investigate rheological properties of the exopolysaccharide, 1% exopolysaccharide solution and 1% xanthan gum solution were analyzed for the changes in viscosity and shear stress depending on shear rate, whose results are summarized in FIG. 5. As shown in FIG. 5, the exopolysaccharide has shown similar pseudoplastic rheological properties to commercially available xanthan gum, moreover, there is almost no difference in steady viscosity between the exopolysaccharide of the invention and xanthan gum.

EXAMPLE 4
Determination of Immunostimulating Activity of the Exopolysaccharide in Vitro Anticancer activities of polysaccharides are not attributable to direct cytotoxicity of tumor cell but rather to indirect cure effect by immunostimulation of the body. In order to measure immunostimulating activity of the exopolysaccharide produced in Example 2, following 3 immunological activities were analyzed.

EXAMPLE 4-1
Immune Cell Proliferation Assay

Figure 6:
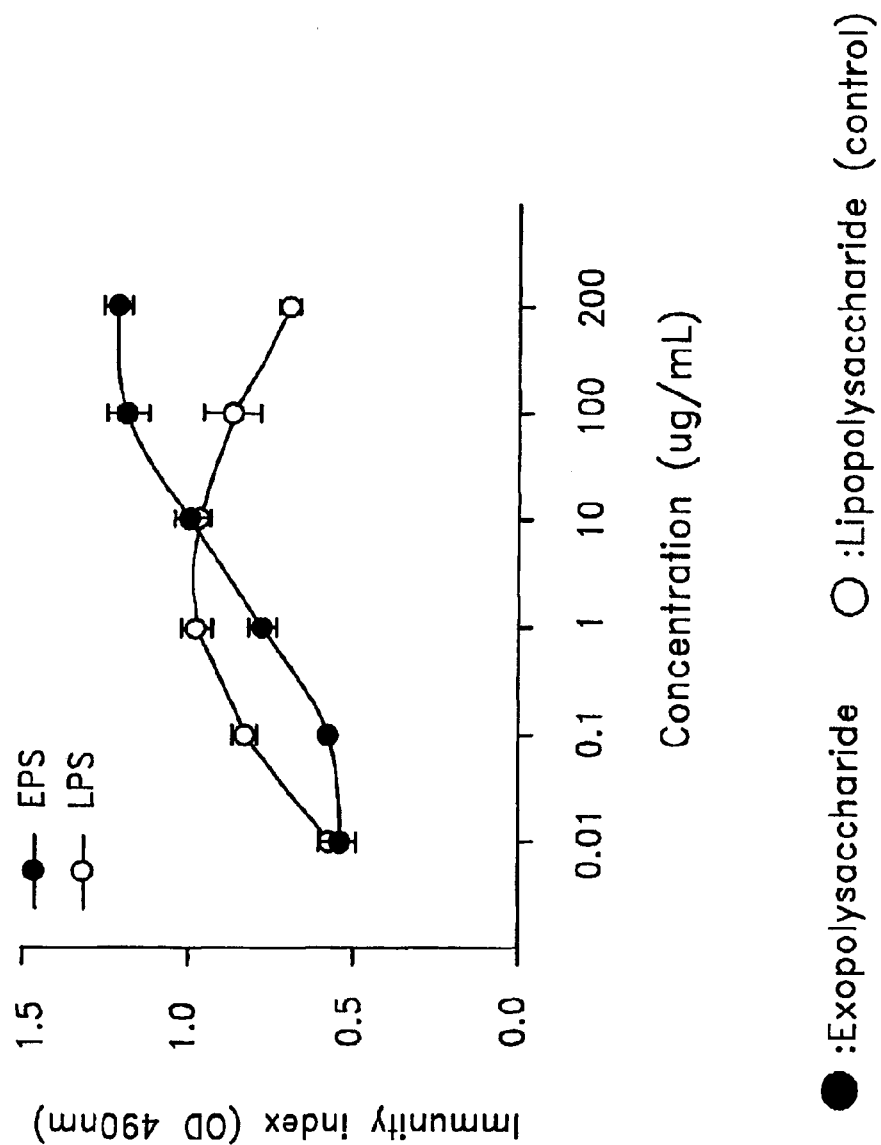
FIG. 6 is a graph showing the growth of immune cells depending on concentrations of the exopolysaccharide.

Following isolation of immune cells from a spleen of Specific pathogen free (SPF) Balb/c mouse, 90 μl aliquots of immune cell suspension were plated into each well of 96-well microtiter plate to a final concentration of $2\times10^6$ cells/ml, and 10 μl each of exopolysaccharide (EPS) solutions were added to the wells to final concentrations of 0.01, 0.1, 1. 10, 100, and 200 μg/ml, respectively. Immune cell growth was determined by incubation of the 96-well plate at 37° C. for 3 days under 5% $CO_2$, followed by measuring absorbancy at 490 nm within 4 hours after adding 20 μl aliquots of MTS solution (see: FIG. 6). As a positive control, lipopolysaccharide (LPS) solution at the same concentration range mentioned above was used.

EXAMPLE 4-2
Mixed Lymphocyte Reaction (MLR)

Figure 7:
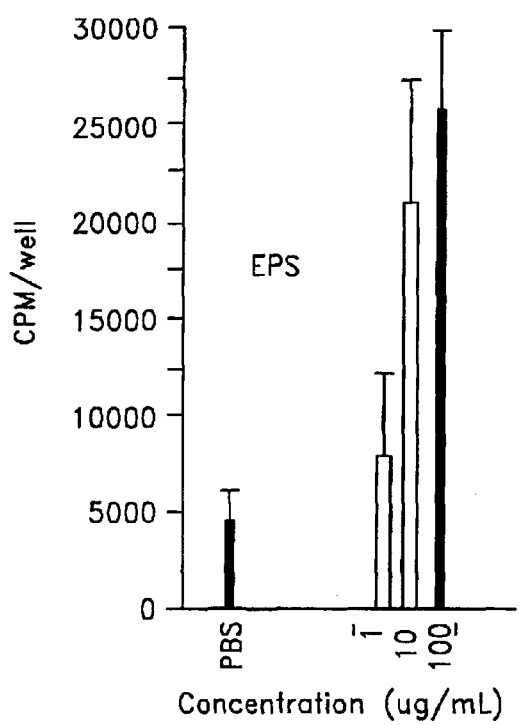
FIG. 7 is a graph showing the effect of exopolysaccharide of the invention on the mixed lymphocyte reaction.

Using spleen cells ($5\times10^6$cells/ml) from SPF B6C3F1(H-2k) mouse and BDF1(H-2d) mouse, mixed lymphocyte reaction (MLR) were induced by addition of the exopolysaccharide of the invention to the final concentrations of 1, 10, and 100 μg/ml, followed by incubation at 37° C. for 3 days under 5% $CO_2$, and then, $^3$H-thymidine absorbed by the cells was counted (see: FIG. 7). As shown in FIG. 7, activity of mixed lymphocytes was increased significantly with EPS treatment compared with control (PBS) group.

EXAMPLE 4-3
Test of Direct Mitogenicity of Immune Cells by EPS

Figure 8:
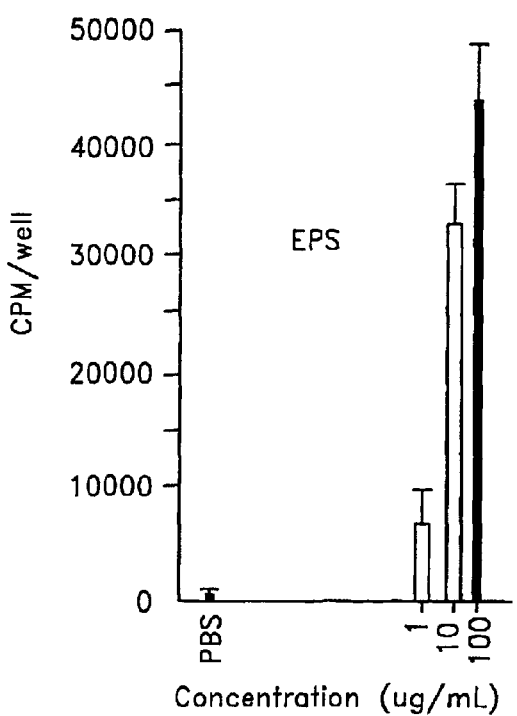
FIG. 8 is a graph showing the mitogenicity of immune cells by exopolysaccharide of the invention.

200 μl aliquots of spleen cells ($1 \times 10^6$ cells/ml) from BDF1 mouse were plated into each well of 96-well plate, and the exopolysaccharide solutions were added to the final concentrations of 1, 10, and 100 μg/ml, followed by incubation at 37° C. for 3 days under 5% $CO_2$, and then, absorption of $^3$H-thymidine by the cells was counted (see: FIG. 8). As shown in FIG. 8, the growth rate of immune cells was increased with increasing the concentration of exopolysaccharide, showing that the exopolysaccharide has mitogenic effect on immune cells.

Figure 9:
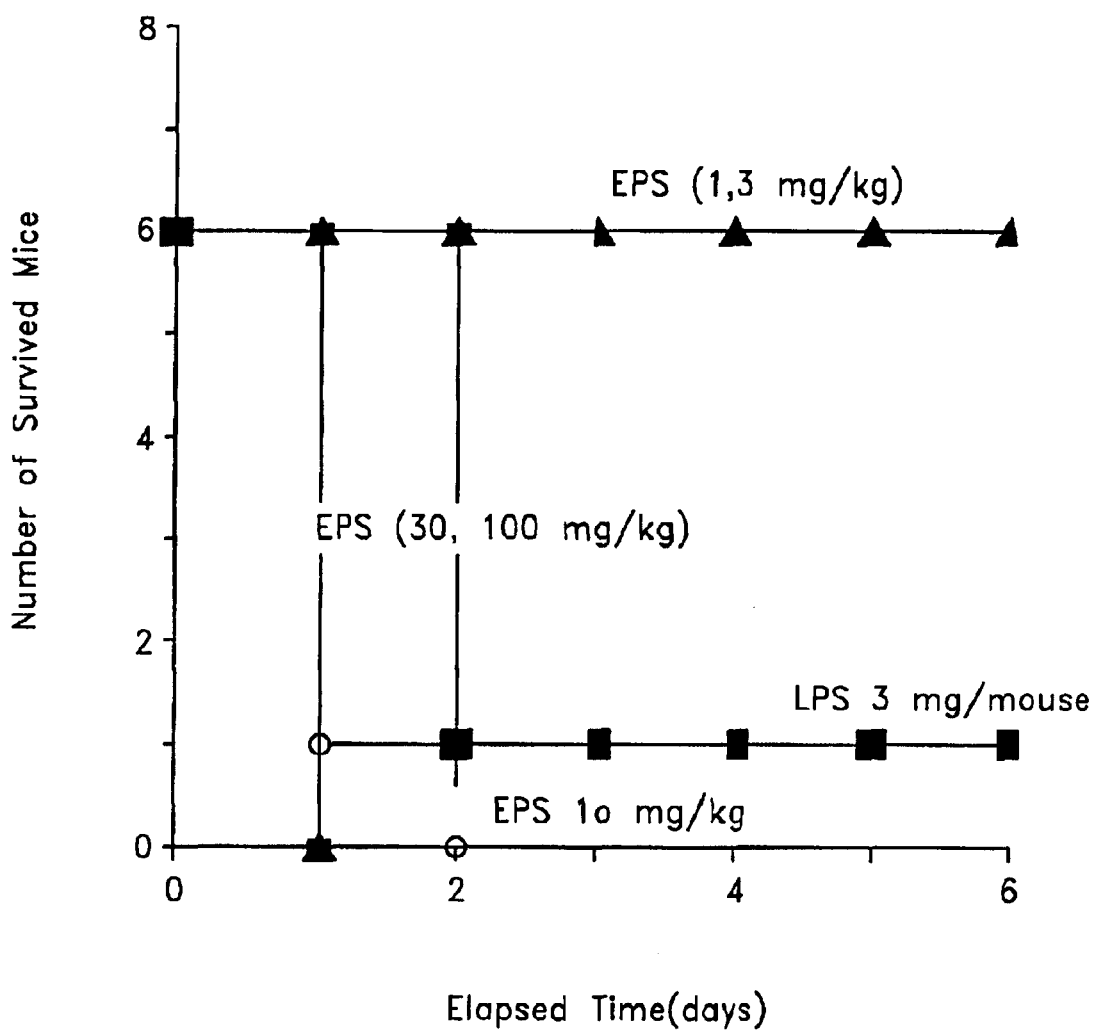
FIG. 9 is a graph showing the acute toxicity of exopolysaccharide of the invention in a septic shock model.

EXAMPLE 5
Test of Acute Toxicity of the Exopolysaccharide in a Septic Shock Model System In order to test the acute toxicity of the exopolysaccharide, septic shock induction was evaluated. In this study, 6 week old SPF female ICR mice obtained from the Korea Research Institute of Bioscience and Biotechnology (Taejeon, Korea) were injected peritoneally with exopolysaccharide solutions at doses of 1, 3, 10, 30, and 100 mg/kg body weight, respectively. Control mice received LPS at dose of 3 mg/mouse (150 mg/kg) in sterilized distilled water. For experiment, 0.2 ml aliquot of EPS or LPS solution per 20 g of body weight were injected peritoneally on day 0. Survived mice were counted until day 6 with checking for death 2 times a day. With exopolysaccharide in dose above 10 mg/kg, there was a toxic shock symptom similar to septic shock, meanwhile, in dose below 10 mg/kg, there was no significant toxicity (see: FIG. 9). Based on these results, anticancer activity of exopolysaccharide by virtue of immunostimulation was measured in doses below 3 mg/kg, e.g., 0.03, 0.1, 0.3, 1, and 3 mg/kg.

EXAMPLE 6
Evaluation of Anticancer Activity of the Exopolysaccharide in a B16 Melanoma Model System In order to evaluate anticancer activity of the exopolysaccharide by virtue of immunostimulation, mice implanted with B16 melanoma cells were used for experiments. SPF BDF1 mice (female, 18–22 g) were obtained from the Korea Research Institute of Bioscience and Biotechnology (Taejeon, Korea). The exopolysaccharide solutions were prepared by dilution with sterile distilled water to doses of 0.03, 0.1, 0.3, 1, and 3 mg/kg. Solvent used for control group was sterile distilled water, and the positive control mice were injected with adriamycin (ADR) at a dose of 1 mg/kg.

Figure 10A:
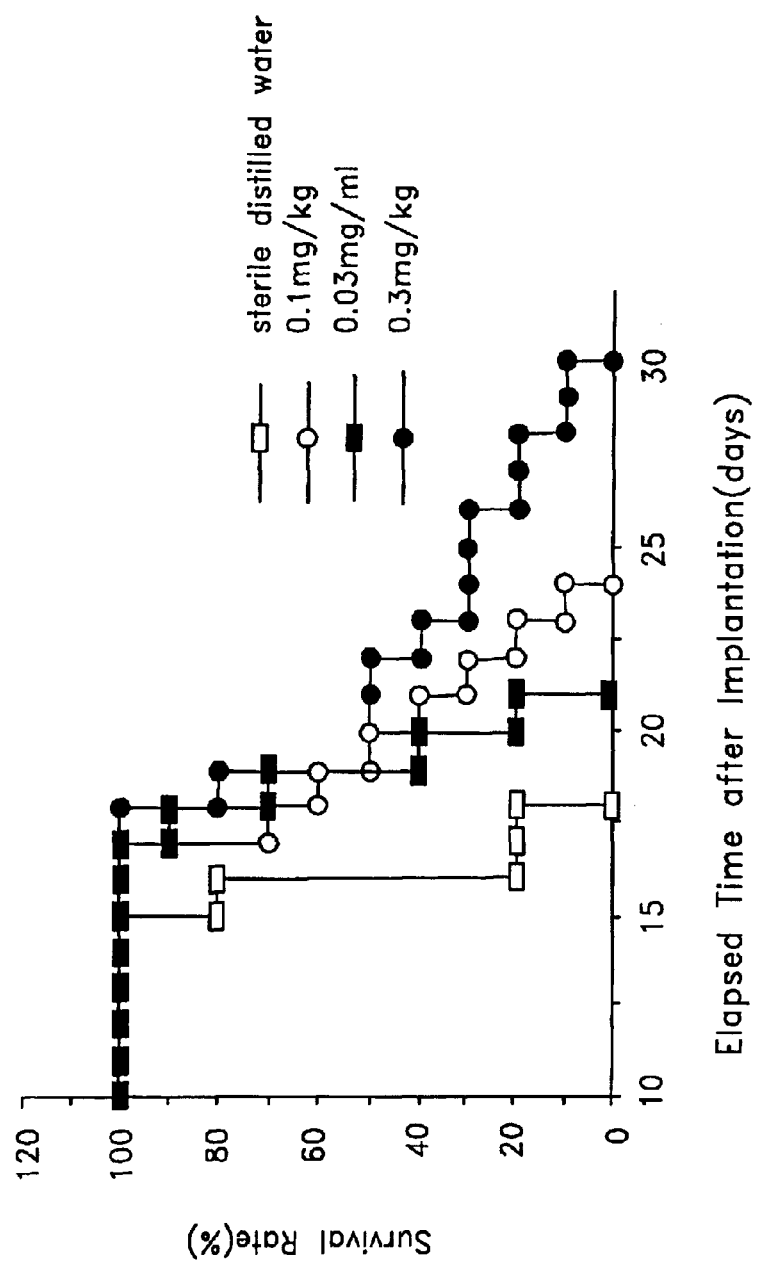
FIGS. 10a and 10b are graphs showing anticancer activity of exopolysaccharide of the invention depending on its concentration in a B16 melanoma model system.
Figure 10B:
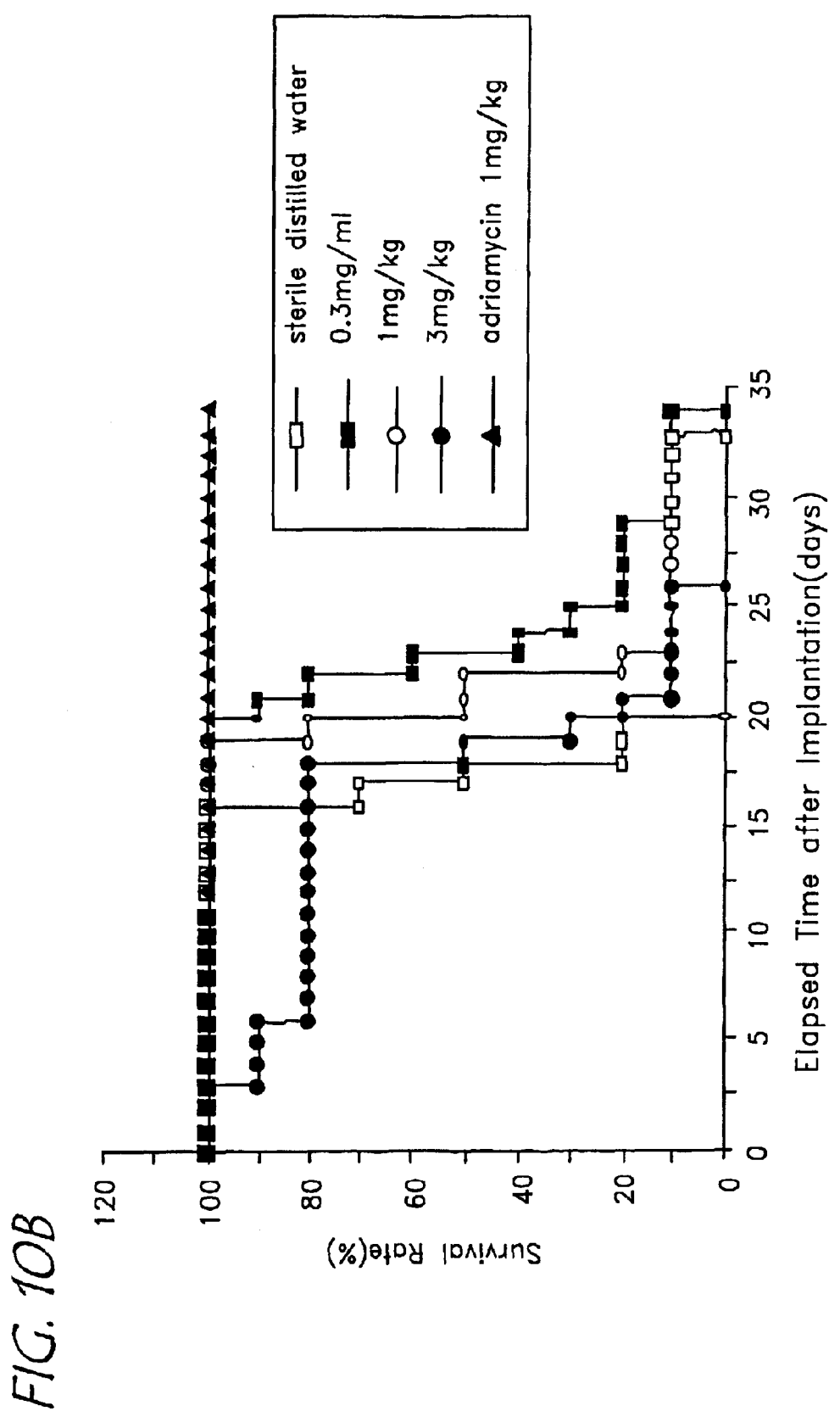

In this study, ten mice were alloted in each group. On day 0, 0.2 ml aliquot of B16 melanoma cell suspension ($1 \times 10^5$ cells/mouse) was implanted intraperitoneally into each mouse, and 4 hours later, the exopolysaccharide prepared above and solvent were injected peritoneally, respectively. Until day 15, EPS were administered with 16 times in total, and daily dosage was 0.2 ml/20 g body weight. Consequently, the exopolysaccharide exhibited considerable anticancer activities of 118.5%, 122.2%, 138.1%, 125%, and 112.5% at concentrations of 0.03, 0.1, 0.3, 1, and 3 mg/kg, respectively, and among them, 0.3 mg/kg group exhibited the highest activity (approximately 140%) (see: FIGS. 10a, 10b). The positive control agent, adriamycin, showed high survival rate of 177.2%.

Figure 11A:
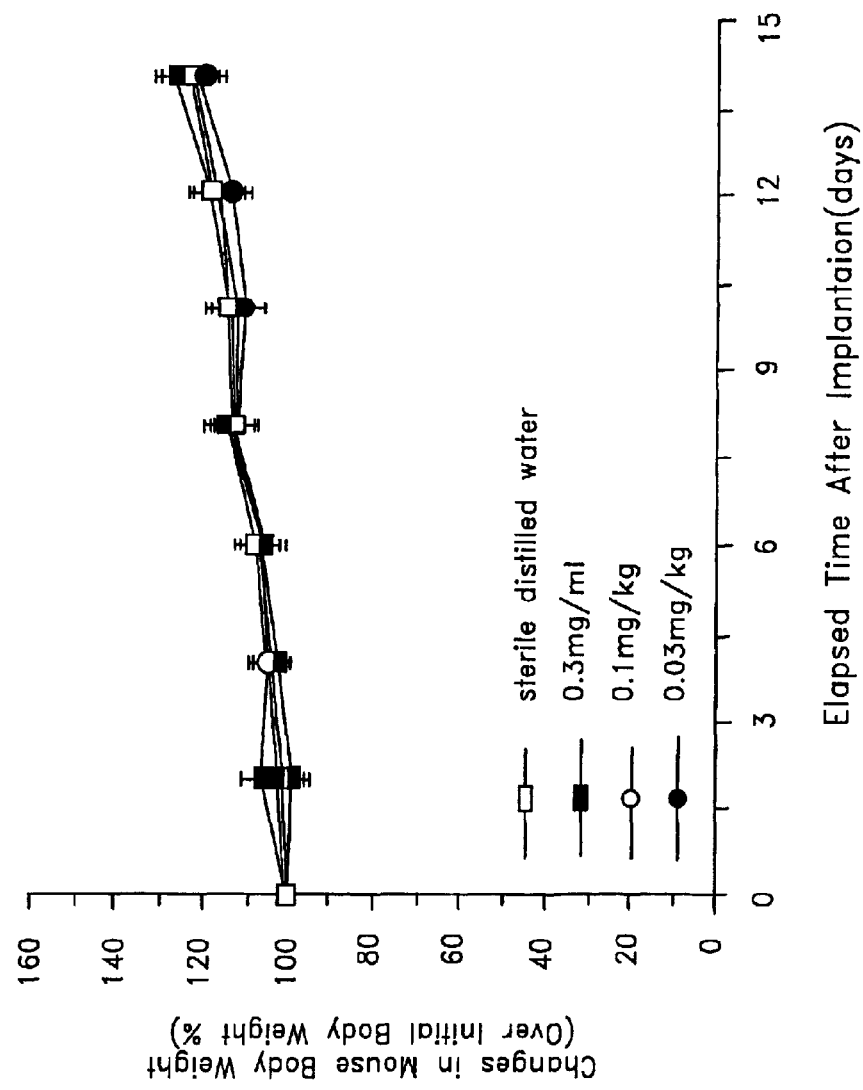
FIGS. 11a and 11b are graphs showing the changes in mouse body weight depending on concentrations of exopolysaccharide during measurement of anticancer activity in vivo.
Figure 11B:
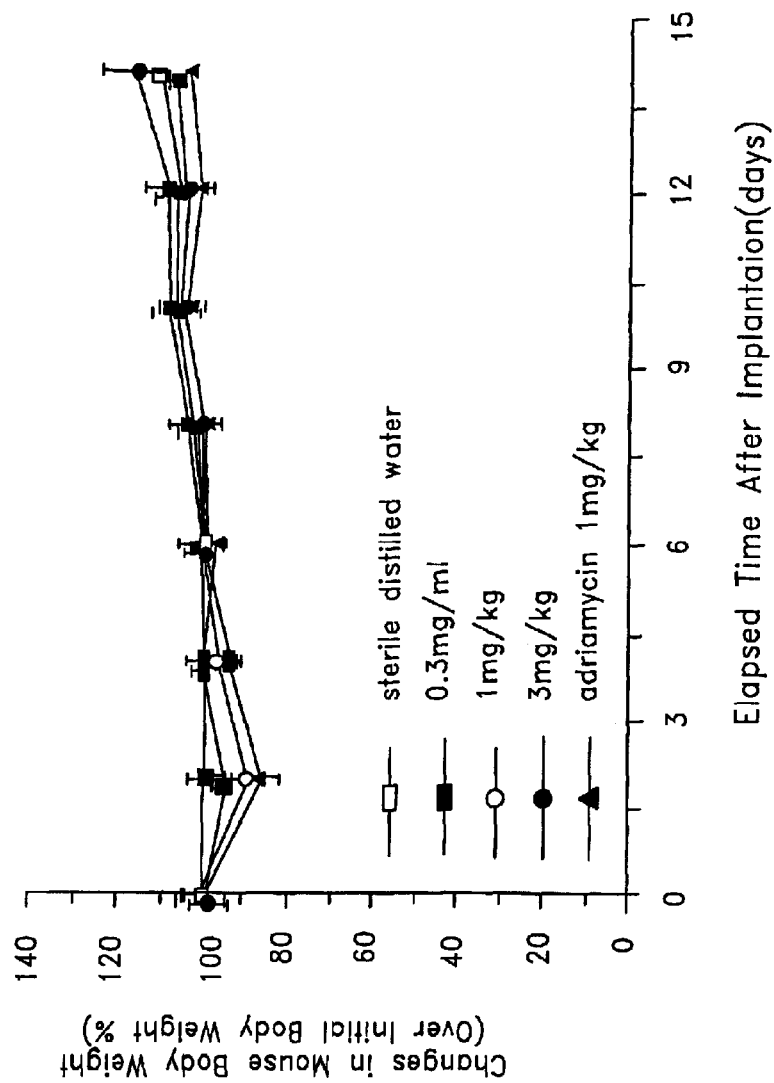

In order to evaluate toxicity of the exopolysaccharide, changes in body weight were examined, and survived mice were counted 2 times a day. The significant reduction in body weight was not observed until 14 days after exopolysaccharide treatment (see: FIGS. 11a, 11b). In solvent control group, death of mice began to be observed on day 15, and on day around 34, all mice in treated groups died except mice in positive control group.

As clearly illustrated and demonstrated above, the present invention provides a novel Enterobacter sp. isolated from Chinese elm alive, which produces immunostimulating exopolysaccharides with anticancer activity, a process for preparing the exopolysaccharides by culturing the said microorganism. In vitro and in vivo assays for immunostimulation revealed that the exopolysaccharide of the invention exhibits anticancer activity by virtue of immunostimulation upon tumors, inflammation, edema, digestive system cancer, leukemia, lymphoma, metastatic cancer, and hepatoma. Therefore, the exopolysaccharide of the invention can be used as an active ingredient of anticancer agents, and as an effective ingredient of immunostimulants for treatment of diseases caused by immune deficiency such as incurable diseases in clinical immunology, cancers, diabetes, male infertility, aquired immunodeficiency syndrome (AIDS), pathogenic viral diseases, and opportunistic diseases, and foodstuffs as well.

What is claimed is:

1. A biologically pure culture of Enterobacter sp. having all of the identifying characteristics of Enterobacter sp. SSYL deposited under accession number KCTC 0687BP.

2. A method of producing an exopolysaccharide, comprising:

providing cells of a biologically pure culture of Enterobacter sp. having all of the identifying characteristics of Enterobacter sp. SSYL deposited under accession number KCTC 0687BP;

culturing the cells in a medium culture so as to allow production of the exopolysaccharide.

3. The method of claim 2, further comprising:

isolating the exopolysaccharide from a mixture comprising the culture medium, the cells and the exopolysaccharide.

4. The method of claim 2, wherein the culture medium comprises a carbon source selected from the group consisting of glucose, sucrose, fructose, rhamnose, galactose, arbinose, mannitol, lactose, gluconate, xylose and mixtures thereof.

5. The method of claim 2, wherein the culturing is performed at a temperature in a range from about 25° C. to about 38° C.

6. The method of claim 2, wherein the culturing is performed under aeration at a flow rate in a range from about 0.1 vvm to about 1.5 vvm.

7. The method of claim 2, wherein the culturing is performed under agitation at an agitation speed in a range from about 150 to about 500 rpm.

8. The method of claim 3, wherein the isolation of the exopolysaccharide comprises:

removing cells from the mixture; and dialyzing a resulting mixture so as to isolate the exopolysaccharide.

9. The method of claim 3, wherein the isolation of the exopolysaccharide comprises:

centrifuging the culture mixture to obtain a supernatant;

precipitating a mixture comprising the exopolysaccharide;

dissolving the precipitate in a liquid; and removing remaining cells.

10. The method of claim 8, further comprising lyophilizing the dialyzed precipitate.

11. A composition comprising the exopolysaccharide obtained by the method of claim 2.

* * * * *